United States Patent [19]

Murakami et al.

[11] Patent Number: 5,019,499

[45] Date of Patent: May 28, 1991

[54] METHOD OF PRODUCING PEPTIDES BY TRANSFORMING MYELOMA CELLS WITH A RECOMBINANT PLASMID

[75] Inventors: Kenji Murakami; Yasuaki Tonooka; Norie Saito; Kokichi Nakasuji; Norifumi Sugiyama, all of Tokyo, Japan

[73] Assignee: Daiichi Seiyaku Co., Ltd., Tokyo, Japan

[21] Appl. No.: 38,177

[22] Filed: Apr. 14, 1987

[30] Foreign Application Priority Data

Apr. 14, 1986 [JP] Japan .................................. 61-85527

[51] Int. Cl.$^5$ .............................................. C12N 15/00
[52] U.S. Cl. .................................. 435/69.1; 435/69.3; 435/69.4; 435/69.5; 435/212; 435/226; 435/240.1
[58] Field of Search ................ 435/68, 70, 172.3, 235, 435/320, 240.1, 69.1, 69.3, 69.4, 69.5, 212, 226

[56] References Cited

U.S. PATENT DOCUMENTS

| | | | |
|---|---|---|---|
| 4,663,281 | 5/1987 | Gillies | 435/69.1 |
| 4,713,339 | 12/1987 | Levinson | 435/240.2 |
| 4,740,461 | 4/1988 | Kaufman | 435/69.1 |

FOREIGN PATENT DOCUMENTS

| | | |
|---|---|---|
| 117058 | 8/1984 | European Pat. Off. . |
| 117059 | 8/1984 | European Pat. Off. . |
| 171496 | 2/1986 | European Pat. Off. . |
| WO86/6058-07 | 10/1986 | PCT Int'l Appl. . |

OTHER PUBLICATIONS

Mulligan et al., *Science*, 209: 1422–1427 (1980).
Kadotani et al., *Seikagaku*, 56, 915 (1984).
Innis, F. et al., 1983, *J. Cellular Biochem.*, S7A:132, Abstract of Meeting presentation.
Gillies, S. D. et al., 1983, *Cell*, 33: 717–728.
Macario, A. J. L. et al., "Monoclonal Antibodies Against Bacteria", vol. 1, Academic Press, p. 211 (1985).
Gray, P. W. et al., *Proc. Natl. Acad. Sci. U.S.A.*, 80:5842–5846 (1983).

*Primary Examiner*—Richard A. Schwartz
*Attorney, Agent, or Firm*—Sughrue, Mion, Zinn, Macpeak & Seas

[57] ABSTRACT

A method of producing desired peptides by transforming mammalian cells and cultivating the transformed cells can be improved by using myeloma cells as the mammalian cells and/or using a vector having the SV40 early promoter sequence on both the 5' upstream and 3' downstream sides of the gene coding for the desired peptide.

6 Claims, 4 Drawing Sheets

METHOD OF PRODUCING PEPTIDES BY TRANSFORMING MYELOMA CELLS WITH A RECOMBINANT PLASMID

FIELD OF THE INVENTION

The present invention relates to a method of producing peptides utilizing genetic engineering technology, a recombinant plasmid for use in the same and animal cells transformed with the same.

BACKGROUND OF THE INVENTION

Various attempts have been made to produce peptides by transforming animal cells and culturing the transformants. Examples thereof are listed below together with the approximately calculated productivities.

(i) BPV (bovine papilloma virus)-mouse C127 system: Human IFN-γ gene (cDNA), SV40 early promoter; $3 \times 10^5$ u/ml (R. Fukunaga et al., Proc. Natl. Acad. Sci. USA, 81, 5086 (1984));

(ii) SV40-CV-1 system: Human IFN-β gene (cDNA), SV40 early promoter; $2 \times 10^4$ u/ml (D. Gheysen et al., J. Mol. Appl. Genetics, 1, 305 (1982));

(iii) SV40-COS system: Human insulin gene (cDNA), SV40 early promoter (O. Laud et al., J. Biol. Chem., 258, 6043 (1983));

(iv) Eco-gpt-CHO system: Human IFN-γ gene (cDNA), SV40 early promoter; $1 \times 10^4$ u/ml (T. Kadotani et al., Seikagaku, 56, 915 (1984)); and (v) dhfr-CHO system: Human IFN-γ gene (cDNA), SV40 early promoter; $1 \times 10^5$ u/ml (S. Scahill et al., Proc. Natl. Acad. Sci. USA, 80, 4654 (1983)).

Although each of these methods has its characteristic features, each method is still unsatisfactory, in particular in the productivity of the desired peptide.

Myelomas have also been used as antibody-producing cells in the production of monoclonal antibody peptides However, their use in the production of other peptides has not yet been known.

SUMMARY OF THE INVENTION

The present invention relates to a method of producing peptides using transformed animal cells, particularly myeloma cells comprises transforming the cells and cultivating the transformed cells. More particularly, in one embodiment, the present invention relates to a method of producing desired peptides which comprises transforming mammalian cells using, as a vector, a recombinant plasmid having the SV40 early promoter sequence on both the 5' upstream and 3' downstream sides of the gene coding for the desired peptide and then cultivating the thus-transformed mammalian cells.

In another embodiment, the present invention relates to a method of producing desired peptide in large quantities comprising transforming myeloma cells with a recombinant plasmid having the SV40 early promoter sequence on both the 5' upstream and 3' downstream sides of the gene coding for the desired peptide is used as a vector.

Myeloma cells are advantageous in that they have the ability to grow rapidly in vivo and in vitro, that they have and a high protein synthesizing capacity (with respect to IgG) and that they are capable of multiplying to a high cell density. An outstanding feature of this embodiment the present invention is that large quantity production of peptides is achieved by the combining the above advantageous features of myeloma cells with the potent expression enhancing effect of the SV40 promoter and enhancer.

Furthermore, the invention relates to a recombinant plasmid having the SV40 early promoter sequence on both the 5' upstream and 3' downstream sides of the gene coding for the desired peptides and to animal cells transformed with said recombinant plasmid.

DETAILED DESCRIPTION OF THE INVENTION

Figure 1:
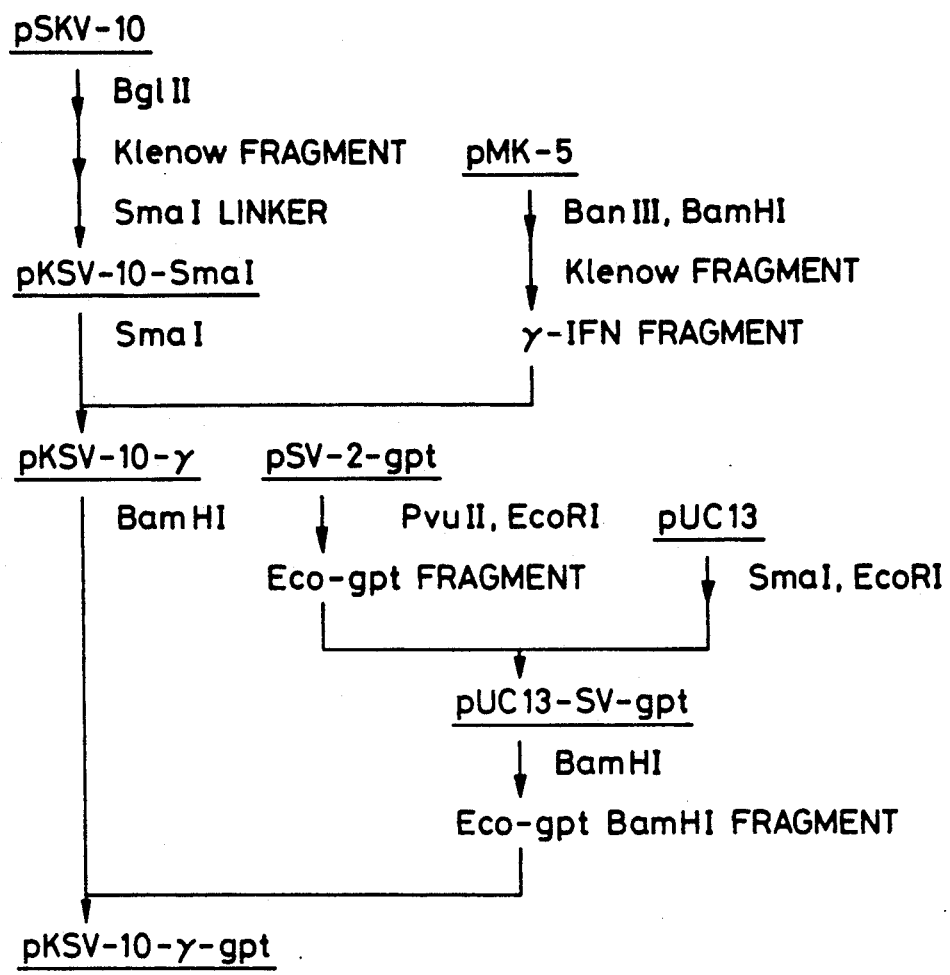
FIG. 1 and FIG. 2 each shows a vector construction scheme.

The SV40 early promoter sequence on the 5' upstream side of the gene coding for the desired peptides should be present within the region of several tens base pairs upstream from the start codon, preferably within several base pairs or immediately upstream from the start codon. Regarding another SV40 early promoter on the 3' downstream side, it is suitable to be present within the region of several kilo base pairs, e.g., 2.5 kbp, downstream from the gene coding for the desired peptides.

The plasmid introduced into the animal cells is incorporated into the animal chromosomal DNA and maintained there stably. The gene product, i.e., peptide is stably produced from the transformed cells and the transformed cells can survive permanently.

The use of non-productive or non-secretory (with respect to IgG) myeloma cells can avoid contamination with IgG, hence is advantageous in purifying the desired peptide. Furthermore, since myeloma cells can be multiplied in the peritoneal cavity of an animal such as a mouse, gene products (peptides) can expectedly by-produced in large quantities.

Another feature of the invention is that the use of a vector with the SV40 promoter positioned at both the 5' upstream and 3' downstream ends of the heterologous gene coding for the desired peptide (e.g., IFN) gives rise to an about 10-fold increase in the productivity of the gene product.

As the cells to be used as host cells, there may be mentioned a variety of myeloma cells, for example mouse, rat and human myeloma cells. Among them, non-IgG-producing or non-IgG-secreting cells are suitable from the product purification viewpoint. The cell lines P3-X63-Ag8-U1 (nonsecretory type) HGPRT$^-$, X63-Ag8-6.5.3 (non-productive type) HGPRT$^-$ and SP2/0-Ag14 (non-productive type) HGPRT- are examples of the mouse myeloma cell lines and are well known (Munemura (ed.): Saibo Baiyo Manual (Manual of Cell Culture), Kodansha, Tokyo (1982); Iwasaki et al.: Tankuron Kotai (Monoclonal Antibodies), Kodansha, Tokyo (1982)).

The vector to be used should suitably have a potent promoter capable of causing gene expression in animal cells (e.g., a SV40 promoter, a BPV promoter, a metallothionein promoter, a dhfr promoter, various long terminal repeat of retrovirus or LTRs all of which are well known) and a selective marker. As the promoter, an SV40 promoter is preferably used. As the selective marker, there may be mentioned, for example, Eco-gpt (as described in Proc. Natl. Acad. Sci. USA, 78, 2072-2076)), tk (as described in Proc. Natl. Acad. Sci. USA, 76, 3757 (1979)) and dhfr (as described in Molec. Cell. Biol., 1, 845-864 (1981)) all of which are well known. Other well known selective markers are also usable.

The base sequence of the SV40 promoter is disclosed in Science, 200, 495-498 (1978). A vector in which the SV40 promoter is combined with the gene for the desired polypeptide can be readily constructed by one of ordinary skill in the art, e.g., by reference to the examples provided below. The cleavage, synthesis, analysis, isolation and other treatments of DNA fragments necessary for vector construction can be conducted by using ordinary techniques. (Am. J. Hum. Genet., 31, 531 (1979); T. Maniatis et al.: Molecular Cloning, Cold Spring Harbor Laboratory (1982)).

The protoplast fusion method, the calcium phosphate method or the like can be employed to transform the animal cells with the recombinant plasmid for introducing the gene in question into the cells. (Mol. Cell. Biol., 1 (8), 743-752 (1981); Proc. Natl. Acad. Sci. USA, 80, 825-829 (1983); Ogawara: Wakariyasui Idenshi Kumikae (Comprehensible Gene Recombination), pp. 144-165, Hirokawa Shoten, Tokyo (1985)).

The cell multiplication can be enhanced in vitro, or in vivo using suitable methods. The cell multiplication system may suitably be selected depending on the case and for the purpose of efficiently producing the desired polypeptide (Iwasaki et al: Tankuron Kotai (Monoclonal Antibodies), Kodansha, Tokyo (1982).

For in vitro culturing, the media which are generally used for culturing myeloma cells in vitro can be used, for example RPMI-1640 medium supplemented with 10% (v/v) fetal calf serum (FCS) or RDF medium (RPMI-1640:DMEM:F12=8:1:1) supplemented with 10% (v/v) of FCS or synthetic serum such as Nu-serum, or serum free media such as RDF medium (RPMI-1640:DMEM:F12=3:1:1) supplemented with ITES (insulin, transferrin, ethanoleamine and selenium) and albumin. (Supplement No. 27 to Tanpakushitsu, Kakusan, Koso (Protein, Nucleic Acid and Enzyme), 453-455 (1984)).

For in vitro cultivation, petri dishes and spinner flasks can be used. As a cultivation method, the high density cultivation method in which cultivation is carried out in a cell density of $10^6$ cell /ml or higher $10^7$-$10^8$) can be used. Specific examples thereof include hollow fiber cultivation (as described in Science, 178, 65 (1972)), microcapsule cultivation (as described in U.S. Pat. No. 4,409,331), air lift cultivation (as described in Briochem. Soc. Trans., 13, 10 (1985)) and membrane perfusion cultivation (the incubator is available from Millipore Co., USA). Among these, the hollow fiber cultivation is efficient and advantageous (the incubator therefor is available from Amicon Co. or Endotronics Co.). The in vitro cultivation may be conducted by well known methods (Munemura (ed): Saibo Baiyo Manual (Manual of Cell Culture), Kodansha, Tokyo (1982) and Fukui et al. (ed.): Saibo Baiyo Gijutsu (Cell Culture Technology), Kodansha, Tokyo (1985)). Thus, for instance, in vitro cell cultivation is carried out in the presence of 5% carbon dioxide.

The in vivo multiplication of myeloma cells may be conducted in the peritoneal cavity of using an animal as is well known in the art. As the animal, there may particularly be mentioned the mouse strain Balb/c nu/nu or Balb/c in which myeloma cell transplantation is possible (these mouse strains are available from Charles River Japan, Inc.).

The present invention is applicable to any kind of useful peptides such as lymphokines such as interferons, tumor necrosis factor and interleukins; hormones such as insulin and growth hormone; antigenic proteins such as hepatitis vaccine and influenza vaccine; tissue plasminogen activator and somatomedins.

The peptide produced can be isolated and purified by an appropriate known methods, e.g., affinity column chromatography, ion-exchange chromatography, molecular sieving, etc..

The following example in which gamma-interferon (γ-IFN) was employed as an example of the peptide will further illustrate the present invention but is by no means limitative of the invention.

EXAMPLE

I. Vector construction (FIG. 1)

a. Insertion of γ-IFN gene into basic veotor

Figure 3:
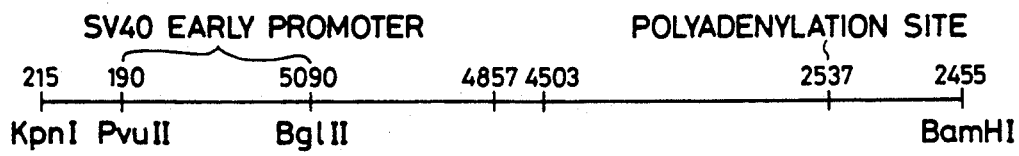
FIG. 3 and FIG. 4 each shows the restriction map of a DNA fragment.
Figure 5:
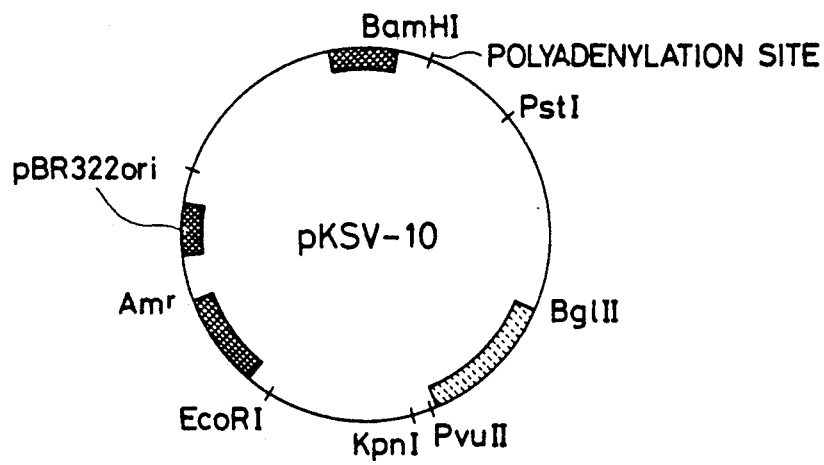
FIGS. 5 to 12 each shows a rough restriction map of each plasmid used.
Figure 6:
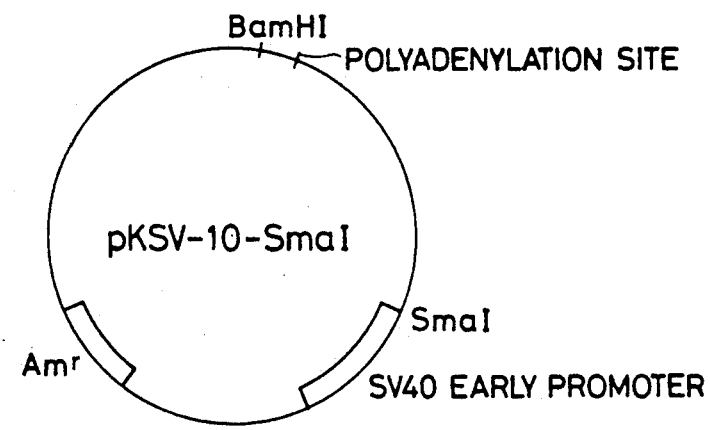

The plasmid pKSV-10 (Pharmacia P-L Biochemicals; see FIG. 5, the restriction map of the KpnI site-BamHI site fragment of this plasmid is shown in FIG. 3) was cleaved at the BglII site immediately behind the SV40 early promoter and made blunt-ended using the Klenow fragment, followed by insertion of a SmaI linker (Takara Shuzo) The thus-obtained plasmid pKSV-10-SmaI (see FIG. 6) was propagated in Escherichia coli HB101.

Figure 7:
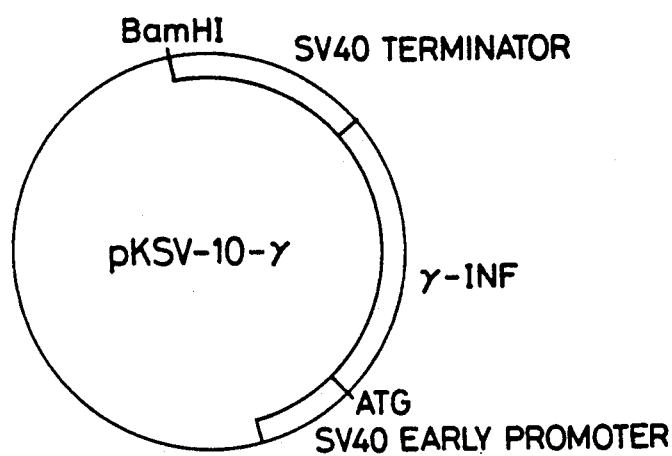
Figure 11:
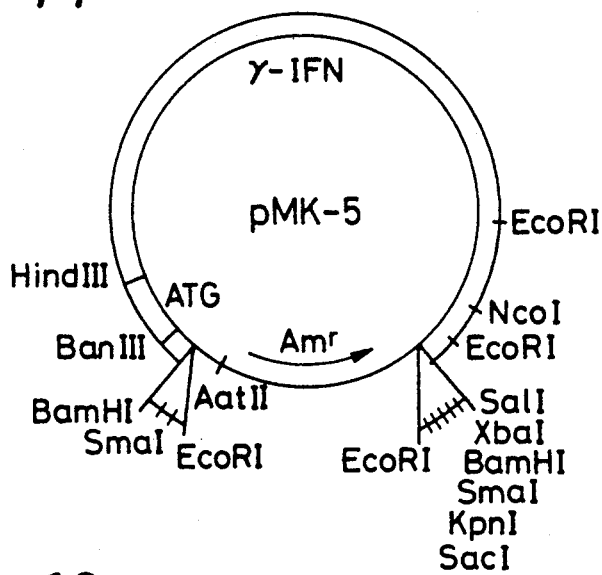

Separately, a human γ-IFN gene-containing plasmid, pMK-5 (deposited at the Fermentation Research Institute in the form of E. coli MK-5; deposition number: FERM BP-1329 (see FIG. 11)), was treated with BanIII and BamHI. The thus-excised γ-IFN gene (genomic) was rendered blunt-ended with the Klenow fragment and inserted into pKSV-10-SmaI at the SmaI site to give pKSV-10-γ (see FIG. 7).

b. Insertion of selective marker Eco-gpt gene into pKSV-10-γ

Figure 4:
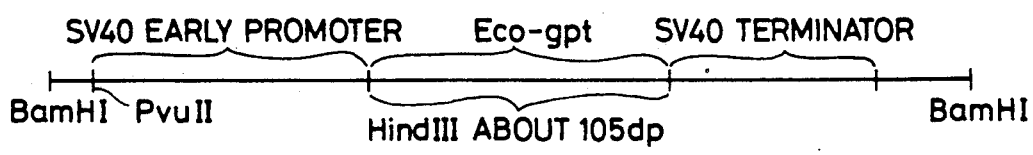
Figure 8:
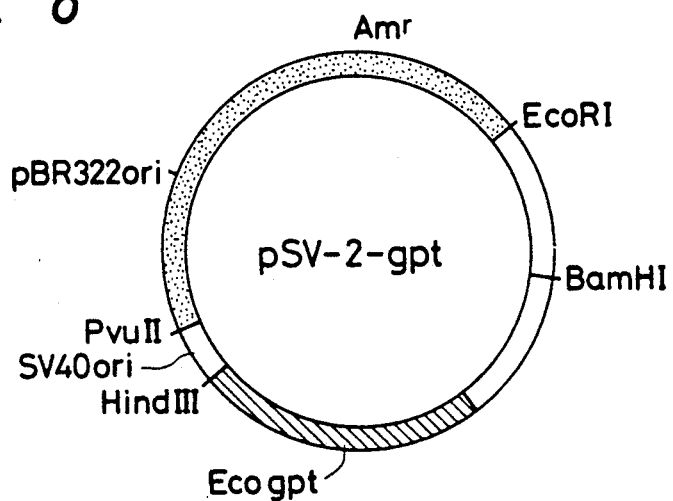
Figure 9:
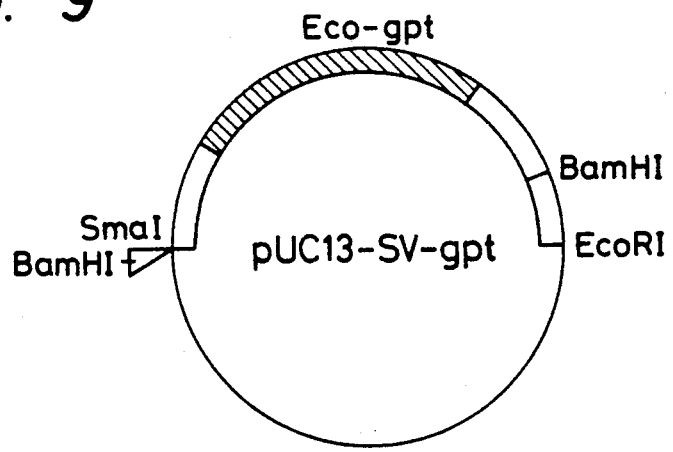
Figure 10:
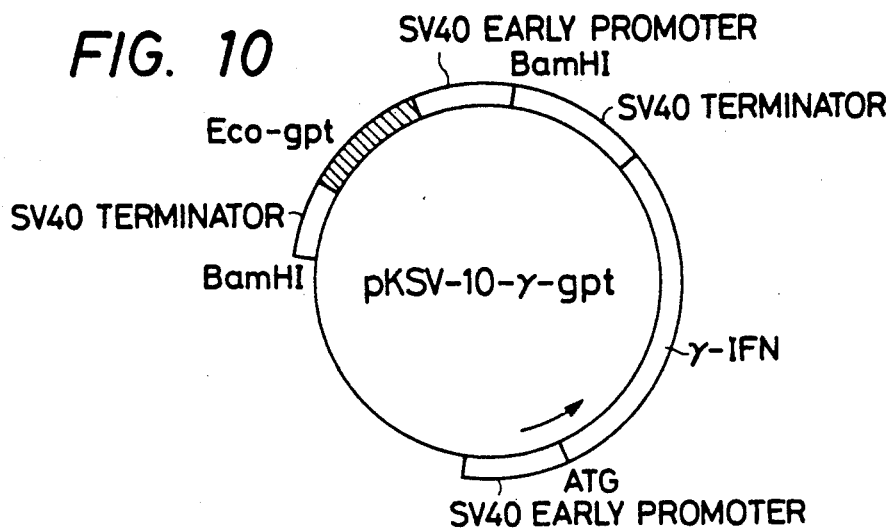

The plasmid pSV-2-gpt (Bethesda Research Laboratories (see FIG. 8) or ATCC No. 37145) was treated with PvuII and EcoRI. The thus-excised Eco-gpt fragment was ligated with the fragment obtained by treating the plasmid pUC13 (Pharmacia P-L Biochemicals) with SmaI and EcoRI, to give the plasmid pUC13-SV-gpt (see FIG. 9). The Eco-gpt gene (SV40 promoter+Eco-gpt+SV terminator) was excised from said pUC13-SV-gpt with BamHI. The resulting fragment, the restriction map of which is shown in FIG. 4, was inserted into pKSV-10-γ (see FIG. 7) (having a BamHI site at the SV40 terminator end on the 3' side of the γ-IFN gene) at the BamHI site to give pKSV-10-γ-gpt (see FIG. 10).

Figure 2:
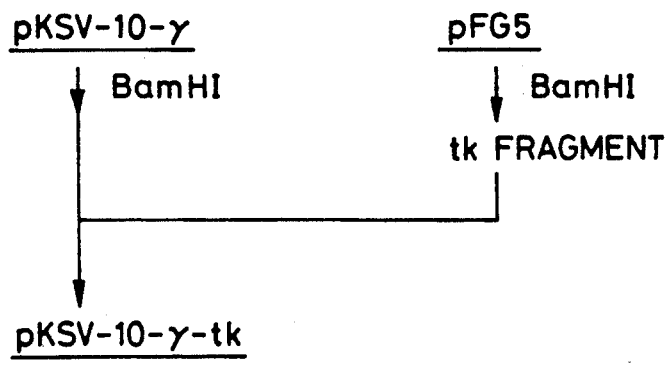

Since the above Eco-gpt gene has the SV40 early promoter on the 5' upstream side, the γ-IFN gene in the plasmid constructed above is in the sandwiched state between two SV40 promoters. This plasmid was used for transformation.

c. Introduction of selective marker tk gene into pKSV-10-γ (see FIG. 2)

Figure 12:
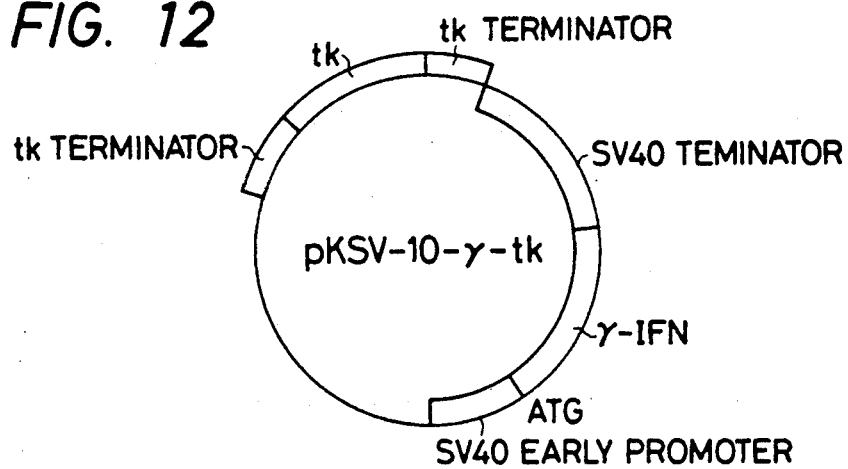

The tk gene (tk promoter+tk+tk terminator) was excised from the plasmid pFG-5 (Proc. Natl. Acad. Sci. USA, 76, 3757 (1979)) with BamHI and inserted into pKSV-10-γ (see FIG. 7) at the BamHI site to give the plasmid pKSV-10-γ-tk (see FIG. 12). This plasmid has only one SV40 early promoter on the 5' side of the γ-IFN gene. This was used for transformation.

II. Establishment of transformed myeloma line a. Plasmid introduction by protoplast fusion (1) Protoplast preparation

*Escherichia coli* carrying the vector pKSV-10-γ-gpt (see FIG. 10) was cultivated at 37° C. in L broth (LB) containing glucose (final concentration 1 (w/v)%) and ampicillin (final concentration 50 ug/ml) (final volume 50 ml) until the turbidity (OD) at 600 nm became 0.5. The subsequent treatments were conducted at 4° C. The culture broth was centrifuged at 3,000 rpm for 15 minutes, the sediment was rinsed with 0.05 M Tris buffer (pH 8) containing 20 (w/v)% of sucrose, 1.25 ml of the same buffer was added and the mixture was stirred. Thereto was added 0.25 ml of lysozyme (Sigma) (dissolved in 0.25 M Tris buffer (pH 8) to 5 mg/ml), and the resulting mixture was allowed to stand for 5 minutes. After further addition of 0.5 ml of 0.25 M EDTA, the mixture was allowed to stand for 5 minutes.

To the above mixture, there was added 0.5 ml of 0.05 M Tris buffer (pH 8), the temperature was raised to 37° C. and the mixture was allowed to stand for 15 minutes. To this was added 10 ml of DME medium supplemented with sucrose (final concentration 10 (w/v)%) and magnesium chloride (final concentration 10 mM). The resulting mixture was allowed to stand at 37° C. for 10 minutes.

(2) Fusion of protoplasts and myeloma cells (preparation of transformed cells)

Myeloma cells ($1 \times 10^7$ cells; X63-Ag8-6.5.3 (HGPRT$^-$)) (Flow Laboratories Inc.-Dainippon Pharmaceutical Co., Ltd.) were added to the culture obtained above in (1). The mixture was centrifuged at 1,500 rpm for 5 minutes. The supernatant was discarded and the sediment was loosened, 0.5 ml of a polyethylene glycol solution (prepared by adding phosphate-buffered physiological saline (PBS) to 9 g of PEG 4000 (Sigma) to make 20 ml) was added slowly to the sediment to thereby suspend the sediment uniformly. After allowing to stand for 1 minute, eight 1-ml portions of DME medium at 37° C. were added to the suspension at 30-second intervals. The entire mixture was centrifuged, and the sediment was suspended in RPMI-XHT medium having the composition given below. The cell suspension thus obtained was distributed into three 96-well plates and incubated for 48 hours.

Composition of RPMI-XHT medium: To RPMI-1640 (Gibco; for 1 liter) were added 36 mg of kanamycin, 120 mg of streptomycin, 250 mg of xanthine, 13.6 mg of hypoxanthine, 3.87 mg of thymidine, 3.5 μg of 2-mercaptoethanol, and 2.0 g of sodium bicarbonate. The entire volume was made 1 liter. To this was added 100 ml of FCS (fetal calf serum).

Transformed cell selection was then carried out by culturing in the above medium supplemented with mycophenolic acid to 6 mg/liter (RPMI-XHMT). After 2 weeks of culture while half of the medium was replaced with a fresh portion at 3-day intervals, the selection was completed.

For L(tk$^-$) cells (thymidine kinase-requiring mouse fibroblast cell as described in Exp. Cell. Res., 31, 297–312), pKSV-10-γ-gpt and pKSV-10-γ-tk were introduced by the calcium phosphate method and selection was performed in the same manner as above using RPMI-XHMT medium and RPMI-HAT medium, respectively.

III. Expression of γ-IFN

The pKSV-10-γ-gpt-transformed myeloma cells X63-Ag8-6.5.3 (HGPRT$^-$) were adjusted to $5 \times 10^4$ cells/ml with a medium having the composition given below. A 20-ml portion of the suspension was placed in a dish, 100 nm in diameter, and cultured in an incubator at 37° C. for 4 days. Cells were collected and placed in a spinner flask at a cell density of $8 \times 10^4$ cells/ml and a culture volume of 100 ml and cultured in a constant-temperature room maintained at 37° C. at a revolution speed of 50 rpm.

Medium composition: In a mixture of 8 volumes of RPMI-1640 (Sigma; for 1 liter), 1 volume of DME (Sigma) and 1 volume of F-12 (Sigma), there were dissolved 25 mM HEPES (Sigma), 4 g glucose, 2 g sodium bicarbonate, 3.5 μg 2-mercaptoethanol, 36 mg kanamycin, 150 mg streptomycin, 250 mg xanthine, 13.6 mg hypoxanthine and 3.87 mg thymidine to make the whole volume 1 liter. To this was added mycophenolic acid for 6 mg/liter. The resulting mixture was further supplemented with 100 ml of NU serum (Collaborative Research).

Starting with day 5, half of the medium was replaced with a fresh portion of the medium every day. Culturing was continued while maintaining the cell density in the spinner flask at $1.0 \times 10^6$ to $1.5 \times 10^6$ per ml. The culture supernatant recovered every day was assayed as described below.

Regarding the transformed L cells obtained in II, they were cultured in 60-mm dishes in the conventional manner and each supernatant was assayed as described below.

Separately, 7-week-old Balb/c nu/nu nude mice were intraperitoneally inoculated with 0.5 ml of pristane (2,6,10,14-tetramethyl-pentadecane; Wako Pure Chemical Industries) and, after 1 week, further inoculated intraperitoneally with $1 \times 10^7$ myeloma cells X63-Ag8-6.5.3 (HGPRT$^-$) transformed with pKSV-10-γ-gpt. After the subsequent 20 days of feeding, the ascitic fluid was collected and assayed as described below.

IV. Assay of γ-IFN

The culture supernatant and ascitic fluid samples were assayed for γ-IFN using 50% cytopathic effect (CPE) inhibition assay in a 96-well microtiter plate, as reported by Philip et al. (Methods in Enzymology, 78, 389–394 (1981)), using human amnion-derived FL cells and SV (Shindbis virus) together with standard α-IFN obtained from NIH and γ-IFN obtained from Genentech's.

The assay results thus obtained are shown below. In vitro culture:

| Vector | Host | γ-IFN titer (u/ml/10$^6$ cells/day) |
| --- | --- | --- |
| pKSV-10-γ-gpt | X63-Ag8-6.5.3 (HGPRT$^-$) | $4 \times 10^5$ |
| pKSV-10-γ-gpt | L (tk$^-$) | $3 \times 10^3$ |
| pKSV-10-γ-tk | L (tk$^-$) | $3 \times 10^2$ |
| Intraperitoneal culture in Balb/c nu/nu mouse: | | |
| pKSV-10-γ-gpt | X63-Ag8-6.5.3 (HGPRT$^-$) | $7 \times 10^5$ |

While the spinner culture cultivation was continued for 20 days, production in half of the medium recovered each day starting with day 5 of cultivation remained almost unchanged. The expression of $4 \times 10^5$ u/ml corresponds to 50 ml medium/100 ml spinner flask/day and is a very excellent one. It is estimated that high density culture using hollow fibers should give an expression of $5 \times 10^7$ u/ml The invention thus provides an excellent method of producing peptides.

Expression of the α-IFN gene which was used in lieu of the γ-IFN gene in the pKSV-10-γ-gpt-L(tk⁻) and pKSV-10-γ-tk-L(tk⁻) combinations gave titers of $1 \times 10^4$ u/ml and $2 \times 10^3$ u/ml, respectively.

When an expression was carried out in the pKSV-10-γ-gpt and X63-Ag8-6.5.3 combination in a spinner culture using a medium which did not contain any serum (containing insulin, transferrin, selenium, ethanolamine and bovine serum albumin (BSA) instead of FCS), $1 \times 10^6$ u/ml of titer was obtained.

What is claimed is:

1. A method of producing desired polypeptides comprising:
   (1) transforming myeloma cells with a vector having the SV40 early promoter sequence on both the 5' upstream and 3' downstream sides of the gene coding for the desired polypeptide;
   (2) cultivating the transformed cells, and
   (3) purifying the desired polypeptide.
2. The method as claimed in claim 1, wherein said myeloma cell is selected from the group consisting of mouse myeloma cells, rat myeloma cells and human myeloma cells.
3. The method as claimed in claim 2, wherein said mouse myeloma cells are selected from the group consisting of P3-X63-Ag8-U1 HGPRT⁻, X63-Ag8-6.5.3 HGPRT⁻ and SP2/O-Ag14 HGPRT⁻.
4. The method as claimed in claim 1, wherein said desired polypeptide is selected from the group consisting of lymphokines, hormones, antigenic proteins, tissue plasminogen activator and somatomedins.
5. A mammalian cell transformed with a vector having the SV40 early promoter sequence on both the 5' upstream and 3' downstream sides of a gene coding for a desired polypeptide, wherein said mammalian cell is a myeloma cell.
6. The mammalian cell as claimed in claim 5, wherein said desired polypeptide is selected from the group consisting of lymphokines, hormones, antigenic proteins, tissue plasminogen activator and somatomedins.

* * * * *